(12) United States Patent
Barker et al.

(10) Patent No.: US 12,053,654 B2
(45) Date of Patent: Aug. 6, 2024

(54) PULSED OXYGEN DELIVERY SYSTEM AND METHOD FOR A CLOSED BREATHING ENVIRONMENT

(71) Applicant: B/E Aerospace, Inc., Winston-Salem, NC (US)

(72) Inventors: John Terence Barker, Overland Park, KS (US); Michael Brumley, Shawnee, KS (US)

(73) Assignee: B/E AEROSPACE, INC., Winston Salem, NC (US)

( * ) Notice: Subject to any disclaimer, the term of this patent is extended or adjusted under 35 U.S.C. 154(b) by 713 days.

(21) Appl. No.: 17/147,162

(22) Filed: Jan. 12, 2021

(65) Prior Publication Data

US 2022/0219022 A1    Jul. 14, 2022

(51) Int. Cl.
*A62B 7/02*    (2006.01)
*A62B 7/14*    (2006.01)
*B64G 6/00*    (2006.01)

(52) U.S. Cl.
CPC .................. *A62B 7/02* (2013.01); *A62B 7/14* (2013.01); *B64G 6/00* (2013.01)

(58) Field of Classification Search
CPC ... A62B 18/0006; A62B 18/02; A62B 18/025; A62B 18/04; A62B 18/084; A62B 18/10; A62B 17/04; A62B 17/008; A62B 9/02; A62B 9/022; A62B 9/027; A62B 7/02; A62B 7/04; A62B 7/06; A62B 7/14; B64G 6/00
See application file for complete search history.

(56) References Cited

U.S. PATENT DOCUMENTS

| | | | | |
|---|---|---|---|---|
| 2,693,180 A | * | 11/1954 | Galeazzi | F16K 15/144 128/201.27 |
| 4,559,939 A | * | 12/1985 | Levine | B64D 11/0632 128/201.15 |
| 5,309,901 A | * | 5/1994 | Beaussant | A62B 17/006 128/201.29 |
| 5,318,018 A | * | 6/1994 | Puma | A62B 17/008 600/20 |
| 6,186,142 B1 | | 2/2001 | Schmidt et al. | |
| 6,245,009 B1 | * | 6/2001 | Travis | A62B 17/006 600/20 |
| 8,733,352 B2 | | 5/2014 | Bailey et al. | |

(Continued)

FOREIGN PATENT DOCUMENTS

EP    2453990 A1    5/2012

OTHER PUBLICATIONS

Extended European Search Report dated Jun. 8, 2022, issued during the prosecution of European Patent Application No. EP 22150385.7.

*Primary Examiner* — Joseph D. Boecker
*Assistant Examiner* — Brian T Khong
(74) *Attorney, Agent, or Firm* — SNELL & WILMER L.L.P.

(57) ABSTRACT

A pulsed oxygen delivery system is disclosed for a closed breathing environment, which includes a source of gaseous oxygen, a phase dilution type oronasal dispensing mask worn by a user in a closed breathing environment defined by a pressure suit, and a pulse control module for delivering a timed and metered bolus of oxygen from the source of gaseous oxygen to the oronasal dispensing mask upon inhalation by the user.

15 Claims, 7 Drawing Sheets

(56) References Cited

U.S. PATENT DOCUMENTS

| | | | |
|---|---|---|---|
| 9,687,503 B2 | 6/2017 | Gibbins et al. | |
| 10,493,304 B2 | 12/2019 | Schrader et al. | |
| 10,864,388 B2 | 12/2020 | Tatarek | |
| 2003/0024529 A1* | 2/2003 | Beizndtsson | A62B 17/006 128/205.27 |
| 2008/0245370 A1* | 10/2008 | Kobziar | A62B 7/14 128/206.21 |
| 2010/0300444 A1 | 12/2010 | Decker et al. | |
| 2013/0081627 A1* | 4/2013 | Bailey | A62B 7/14 128/204.26 |
| 2013/0312743 A1* | 11/2013 | Kshirsagar | A62B 7/14 128/204.23 |
| 2013/0340760 A1* | 12/2013 | Brumley | B64D 11/00 128/204.29 |
| 2015/0174359 A1 | 6/2015 | Elliott et al. | |
| 2015/0196245 A1* | 7/2015 | Peake | A62B 7/14 128/202.13 |
| 2016/0303405 A1* | 10/2016 | Elliott | A61B 5/0816 |
| 2018/0228997 A1 | 8/2018 | Krentler et al. | |
| 2019/0224505 A1* | 7/2019 | Walker | A62B 7/14 |
| 2021/0069532 A1* | 3/2021 | Jason | A62B 7/14 |

\* cited by examiner

PULSED OXYGEN DELIVERY SYSTEM AND METHOD FOR A CLOSED BREATHING ENVIRONMENT

BACKGROUND OF THE INVENTION

1. Field of the Invention

The subject invention is directed to a pulsed oxygen delivery system, and more particularly, to system and method for delivering a pulsed bolus of oxygen to the lungs of a user shortly after the start of inhalation in a closed breathing environment, such as, for example, a pressure suit worn by an astronaut that is required to support extravehicular activities outside of a spacecraft.

2. Description of Related Art

The pulsed delivery of supplemental oxygen to a user by way of a phase-dilution mask offers known benefits in terms of oxygen utilization efficiency as compared with a continuous flow of oxygen or that sources from the ambient environment, that being administered either at ground level conditions or most notably in low partial pressure environments. These benefits are due to a controlled bolus of oxygen being delivered directly to the lungs shortly after the start of inhalation rather than regions that do not support diffusion of oxygen to the blood stream. In addition, the delivery of the bolus of oxygen in a low ambient pressure environment is such that the volume of oxygen expands significantly to more completely fill the user's lungs, as compared with normal respiration. Such an effect is particularly noticeable at pressures less than 5.45 psia or 25,000 ft. equivalent.

The pulsed dispensing of supplemental and therapeutic oxygen is therefore widely practiced in the commercial aviation industry where the weight and volume occupied by the oxygen storage and supply system are important considerations, as disclosed for example in U.S. Pat. No. 8,733,352. That said, it would be beneficial to provide a pulsed oxygen delivery system for use in a closed breathing environment such as, for example, in a pressure suit worn by an astronaut performing extravehicular activity outside of a spacecraft.

SUMMARY OF THE DISCLOSURE

The subject invention is directed to a new and useful pulsed oxygen delivery system for a closed breathing environment, a source of gaseous oxygen, a phase dilution type oronasal dispensing mask worn by a user in a closed breathing environment defined by a pressure suit, and a pulse control module for delivering a timed and metered bolus of oxygen from the source of gaseous oxygen to the oronasal dispensing mask upon demand by the user (i.e., shortly after the start of inhalation).

The pulse control module includes a pressure manifold having one or more breath sensors for sensing a breath taken by the user and one or more control valve for controlling the duration and amount of oxygen delivered to the dispensing mask. The source of gaseous oxygen includes a pressurized single use storage vessel or a refillable storage vessel, an initiator or mechanical valve for activating or otherwise establishing the flow of oxygen from the storage vessel and a regulator for managing the delivery of oxygen from the storage vessel to the pressure manifold.

The storage vessel includes a manifold body defining a first flow passage containing a frangible rupture disc, and the initiator includes an initiator body defining a second flow passage in fluid communication with the first flow passage. Means are provided for rupturing the rupture disc to initiate the flow of oxygen from the storage cylinder to the dispensing mask by way of a supply tube.

In one embodiment of the invention, the means for rupturing the rupture disc includes an initiator lance and a pyrotechnic charge for causing the lance to rupture the disc. Alternatively the means for initiating the flow of oxygen could be a mechanical or spring-loaded lance, or the storage vessel could include an oxygen supply valve that is manually or electrically moved from a closed positon to an open positon to initiate the flow of oxygen from the storage vessel. Preferably, the flow of oxygen from the storage vessel is initiated upon the sensing of a valid first breath by the breath sensor, and in the absence of a valid first breath the initiator is activated manually by the application of electrical power.

The pulse control module includes a microcontroller unit that is in communication with the pressure manifold, the source of gaseous oxygen and the pressure suit over an electronic interface. The microcontroller unit is programmed to monitor suit pressure and temperature, manifold pressure and temperature, and storage vessel pressure and temperature. The microcontroller unit is further programmed to manage the initiator or state of the oxygen supply valve, the one or more control valves and the one or more breath sensors. Preferably, the pulse control module is powered by primary and secondary power supplies that are isolated and protected from one another.

The subject invention is also directed to a method for delivering pulsed oxygen to an enclosed oxygen pressurized breathing environment, which involves providing a source of gaseous oxygen, connecting the source of gaseous oxygen to a phase dilution type oronasal dispensing mask worn by a user in a closed breathing environment defined by a pressure suit, and delivering a controlled bolus of oxygen from the source of gaseous oxygen to the oronasal dispensing mask upon demand by the user. Preferably, the controlled bolus of oxygen is delivered shortly after the start of inhalation.

It is envisioned that bolus volume can be controlled in one or more ways. For example, bolus volume could be controlled according to ambient pressure within the pressure suit, bolus volume could be controlled according to oxygen supply pressure and temperature, and/or bolus volume could be controlled according to a user's level of oxygen blood saturation.

Bolus volume could also be controlled so as to maintain a user's level of oxygen blood saturation in a target range equal to or greater than a defined baseline percentage specific to the user, so as to optimize the volume of oxygen that is required to be dispensed, as disclosed for example in commonly assigned U.S. Patent Application Publication No. 2015/0174359, the disclosure of which is incorporated herein by reference. In this regard, the level of blood oxygen saturation could also be measured by an oximeter or similar means and that information could be sent to the microcontroller unit to control the bolus of oxygen delivered to the user.

These and other features of the pulsed oxygen delivery system and method of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those having ordinary skill in the art will readily understand how to make and use the pulsed oxygen delivery system of the subject invention without undue experimentation, preferred embodiments thereof will be described in detail herein below with reference to the figures wherein.

DETAILED DESCRIPTION OF THE PREFERRED EMBODIMENTS

Figure 1:
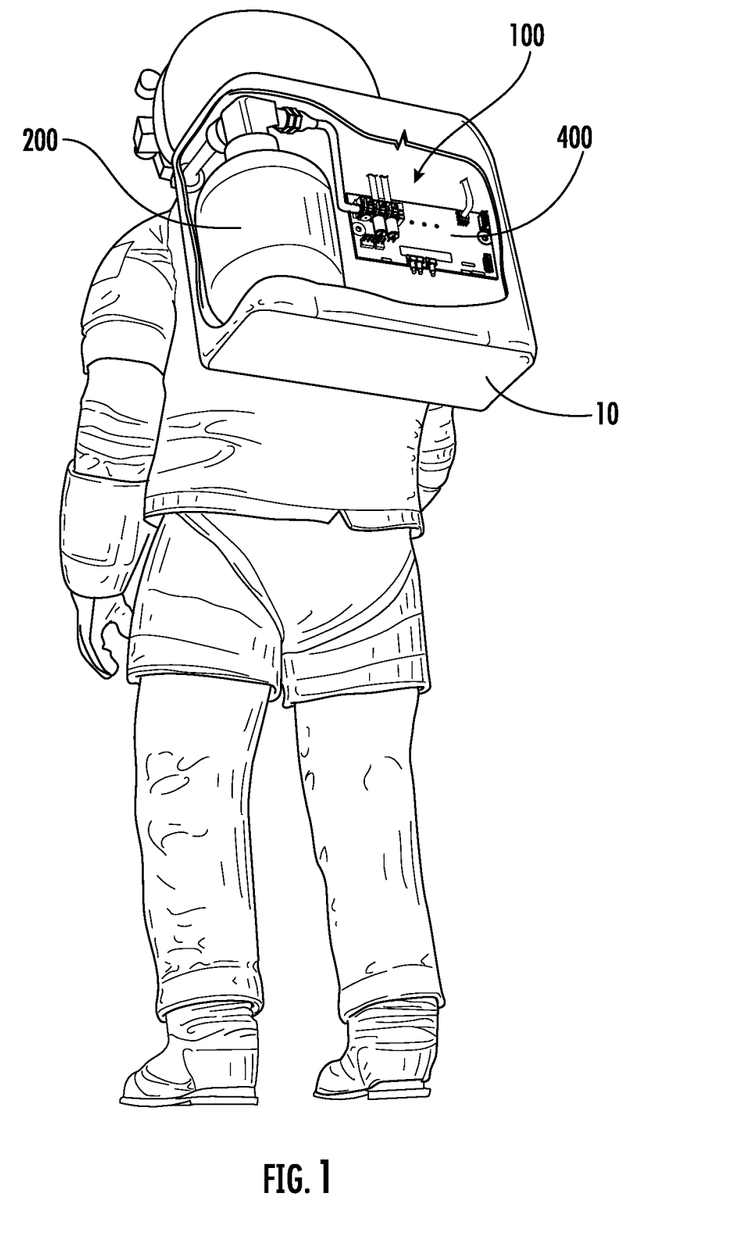
FIG. 1 is a perspective view of a pressure suit defining a closed breathing environment with which the pulsed oxygen delivery system of the subject invention is employed.

Referring now to the drawings wherein like reference numerals identify similar structural features or elements of the subject invention, there is illustrated in FIG. 1 a closed system breathing environment in the form of a pressure suit 10 with which the pulsed oxygen delivery system 100 of the subject invention is employed. The pressure suit 10 is of the type worn by an astronaut performing extravehicular activities outside of a spacecraft.

As discussed in more detail below with reference to FIG. 2, the pulsed oxygen delivery system 100 includes a source of gaseous oxygen 200, an oronasal dispensing mask (i.e., a phase dilution mask) 300 worn by a user in the closed breathing environment defined by pressure suit 10, and a pulse control module 400 for delivering a timed and metered bolus of oxygen from the source of gaseous oxygen 200 to the oronasal dispensing mask 300 upon demand by the user. Those skilled in the art will readily appreciate that the oronasal mask 300 includes an oral-nasal face piece, inhalation and exhalation valves, and a flexible supply tube that connects the mask 300 to the pulse control module 400, as described in more detail below with reference to FIG. 8.

The pulsed oxygen delivery system 100 is adapted and configured to respond to inhalation by delivering a precisely metered bolus volume (pulse) of oxygen directly to the lungs by way of mask 300 shortly after the start of inhalation in preference to regions that do not support diffusion of oxygen to the blood stream. As discussed in more detail below, this bolus volume of oxygen can be varied according to suit pressure conditions or in direct response to actively measured blood oxygen (pulse) saturation $SpO_2$ levels of the user. The efficiency of the system depends on delivering the pulse early in the inhalation cycle. In order to maintain this level of efficiency, it is important to ensure that the inhalation is detected and pulse delivered in a reliable and timely manner.

Figure 2:
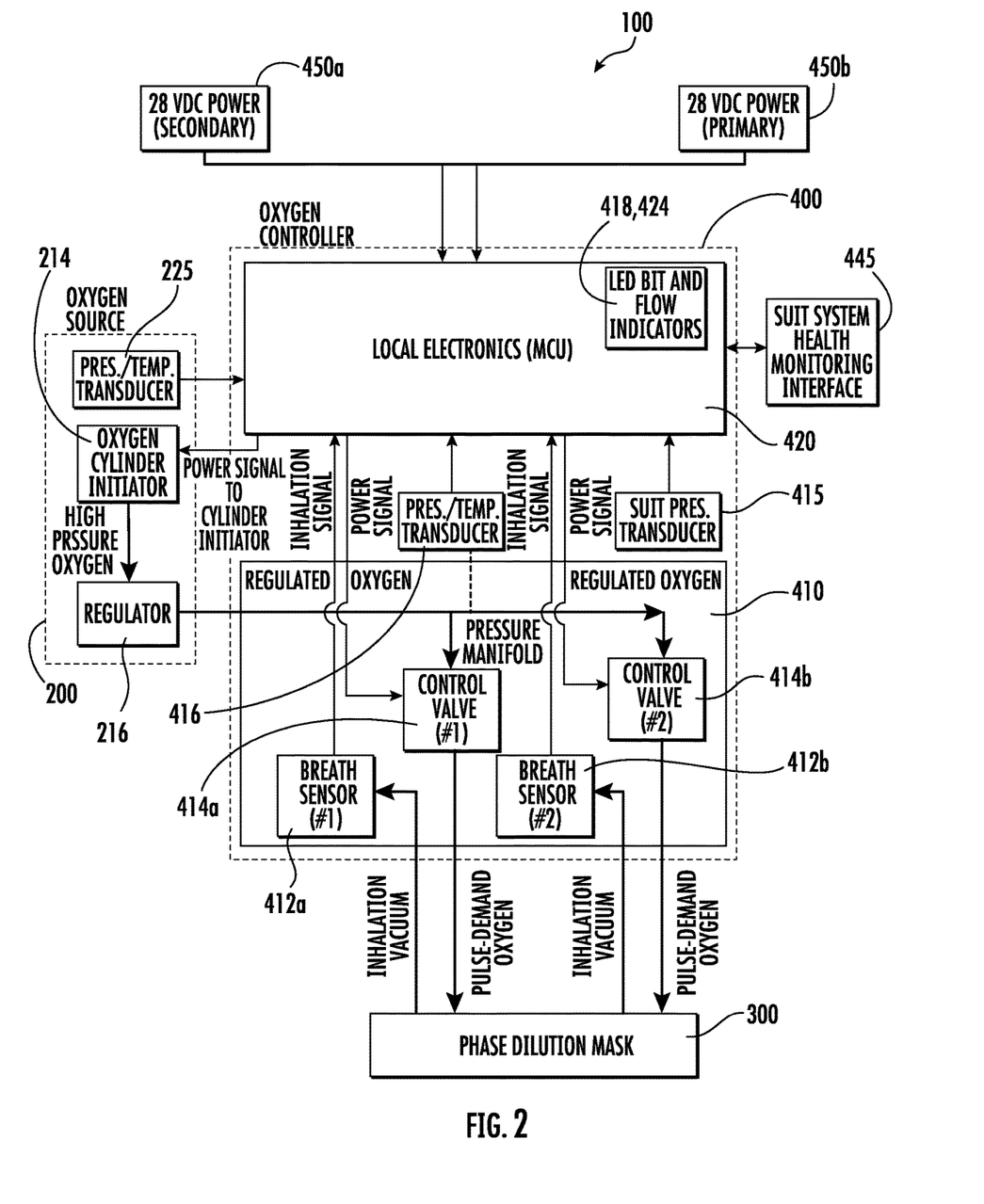
FIG. 2 is a schematic representation of the pulsed oxygen delivery system of the subject invention.
Figure 6:
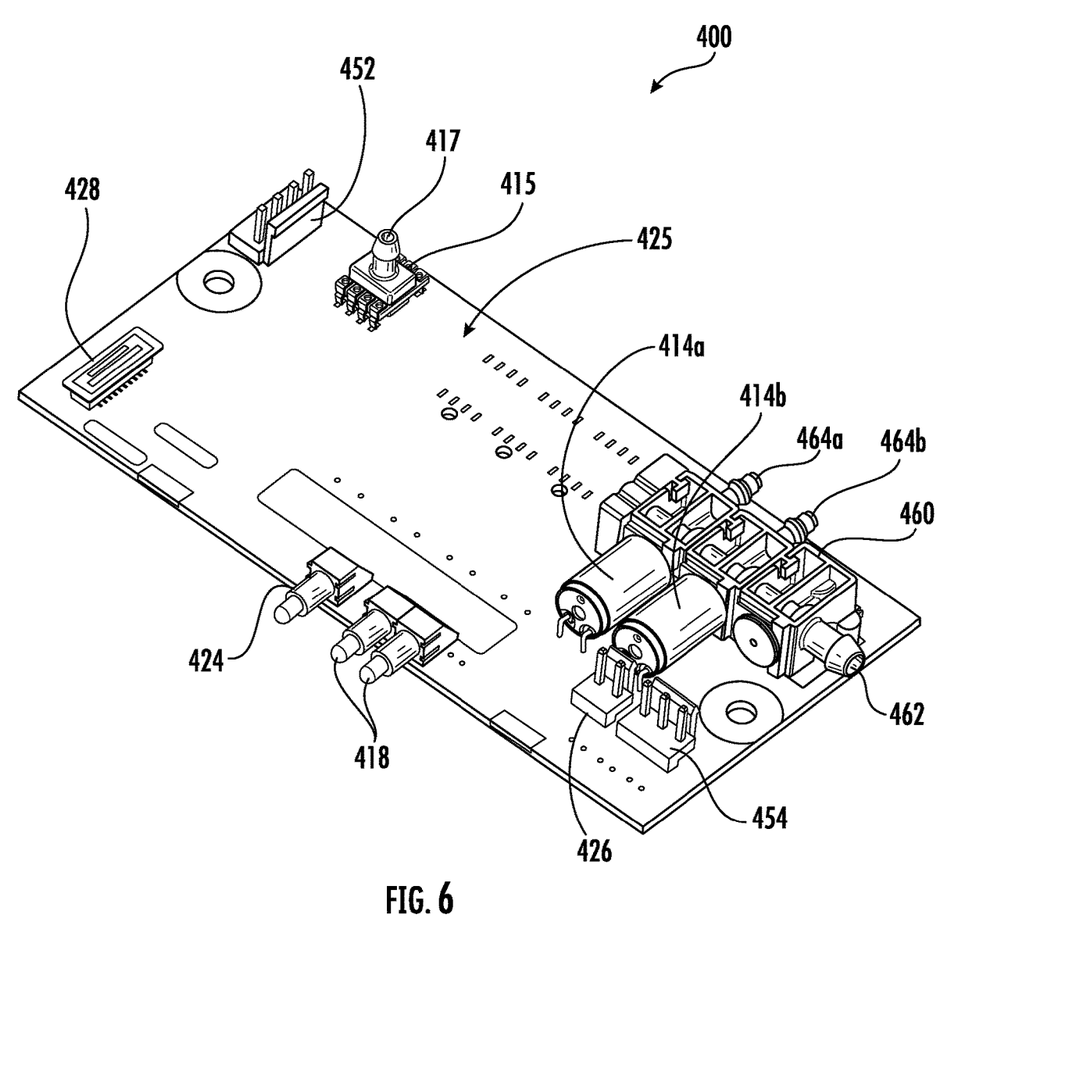
FIG. 6 is a perspective view oxygen controller assembly shown in FIG. 1.

Referring now to FIG. 2 in conjunction with FIG. 6, the pulse control module 400 is adapted and configured to perform monitor and control function by way of a microcontroller unit (MCU) 420, which includes an electronics package that employs software. It resides on a circuit board 425 that is preferably manufactured from fiberglass reinforced epoxy, where the circuitry is silk-screened using a solder mask that is conformally coated. The circuit board 425 includes a programmable port 428 for uploading instructions and data to the MCU 420.

The pulse control module 400 further includes a pressure manifold 410 and an electronic microcontroller unit 420. The pressure manifold 410 includes a manifold housing 460 that acts as a plenum on the circuit board 425 for distributing oxygen to the user. The manifold housing 460 has an inlet 462 for receiving oxygen from the supply source 200 and a pair of outlet fittings 464a, 464b for communicating with the oronasal mask 300 by way of associated tubing.

The pressure manifold 410 further includes a pair of breath sensors 412a, 412b, which act as a vacuum pressure switches for sensing a breath taken by the user, and a pair of solenoid control valves 414a, 414b for controlling the duration and amount of oxygen delivered to the dispensing mask. Inhalation demand is sensed by the breath sensors 412a, 412b as a small differential pressure in the supply tube created by inhaling through the mask 300. The solenoid control valves 414a, 414b are characterized as 2-way, normally closed with a nominal 20 ms on-off response time. The paired breath sensors and control valves provide for parallel redundant operation of the system.

The effective bolus volume is determined by the duration that the dispensing solenoid valve 414a, 414b is open. Upon sensing a breath, the controller 400 opens the solenoid valve 414a, 414b to provide a small, metered pulse of oxygen. The controller 400 meters the quantity of oxygen by adjusting the duration that the valve is powered open. This duration is calculated based on the results of a series of equations or by a look up table that reflects the characteristics and response of the dispensing system, but is controlled based on the current suit pressure or the user's $SpO_2$ levels.

With continuing reference to FIGS. 2 and 6, the oxygen control module 400 employs a board mounted solid state MEMs absolute pressure sensor 416 to determine suit pressure and temperature. The pressure measurement is compensated in software for sensor specific coefficients and offsets that are pressure and temperature dependent. In the absence of valid data from the suit pressure sensor 416, the system defaults to a pre-defined pulse duration basis (IPW).

Manifold gas temperature and absolute pressure is monitored by an integrated circuit sensor 415 that is mounted on the controller printed circuit board 425. A sensing port 417 in the pressure manifold 410 transmits manifold gas directly to that sensor. An LED status indicator array 418 is integrated into the controller board 425, which illuminates to indicate that a breath was taken on the mask 300 and oxygen was dispensed to that mask.

Figure 3:
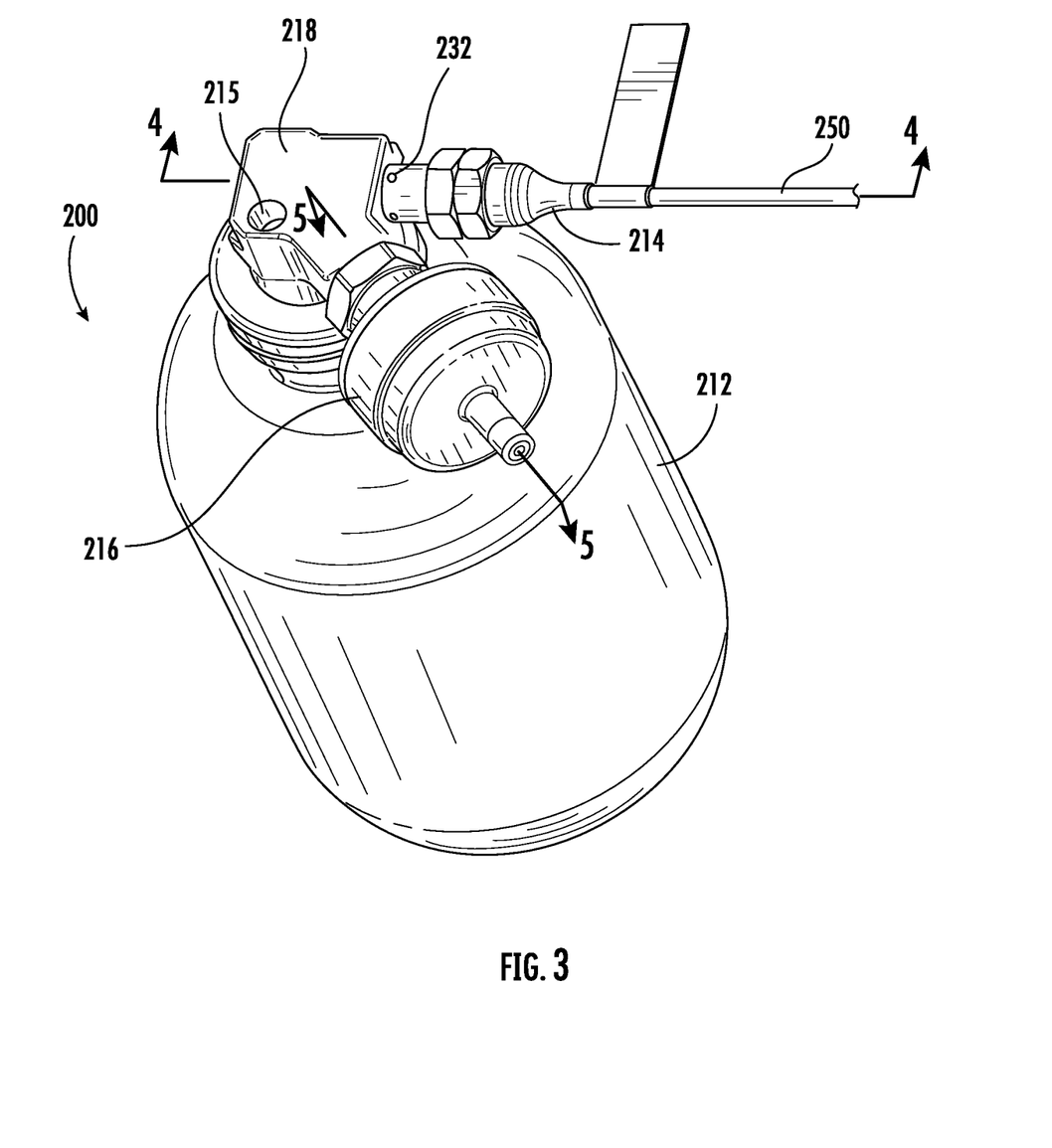
FIG. 3 is a perspective view of the oxygen supply assembly shown in FIG. 1.

Referring now to FIG. 2 in conjunction with FIG. 3, the source of gaseous oxygen or oxygen supply assembly 200 provides a means by which high pressure oxygen is maintained for supply at a regulated pressure that is less than storage pressure. It includes a pressurized single use storage vessel 212, an initiator 214 for activating the flow of oxygen from the storage vessel and a regulator 216 for managing the delivery of oxygen from the storage vessel 212 to the pressure manifold 410. The initiator 214 communicates with the MCU 420 by way of a connector 454 on circuit board 425 shown in FIG. 6

The storage vessel 212 is preferably a non-refillable, single use device, which may be manufactured from a welded stainless steel liner that is structurally supported by a Carbon Fiber Epoxy composite wrapping that is intended to be resistant to outgassing in a persistent low ambient pressure environment. The breathing gas contained in the storage vessel 212 is preferably an oxygen/helium mixture comprising 99.5% oxygen and between 0.25% and 0.50% helium. The helium is used as a challenge gas to perform acceptance leakage tests that verifies the seal between the initiator 214 and the storage vessel 212. The resulting breathing gas mixture provides satisfactory supplemental oxygen for hypoxia protection.

Figure 5:
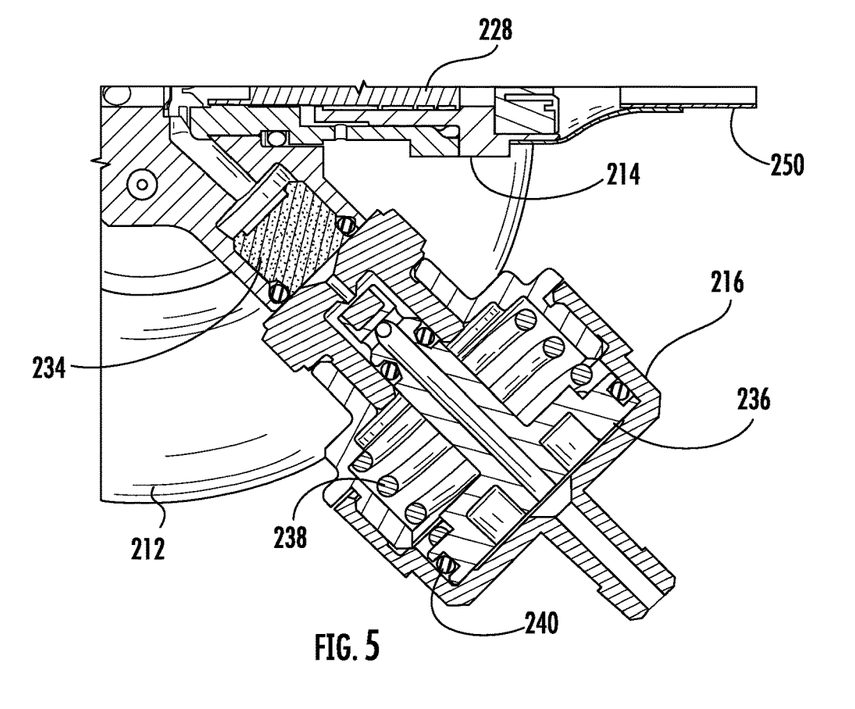
FIG. 5 is an enlarged cross-sectional view of the manifold and pressure regulator assembly taken along line 5-5 of FIG. 3.

As best seen in FIG. 5, pressure regulation is provided by a mechanical single stage piston type regulator 216. The inlet of the regulator 216 is protected by a porous sintered bronze filter 234, and pressure is regulated by way of an aluminum piston 236 under the bias of a stainless steel spring 238 and sealed by an O-ring 240.

Figure 4:
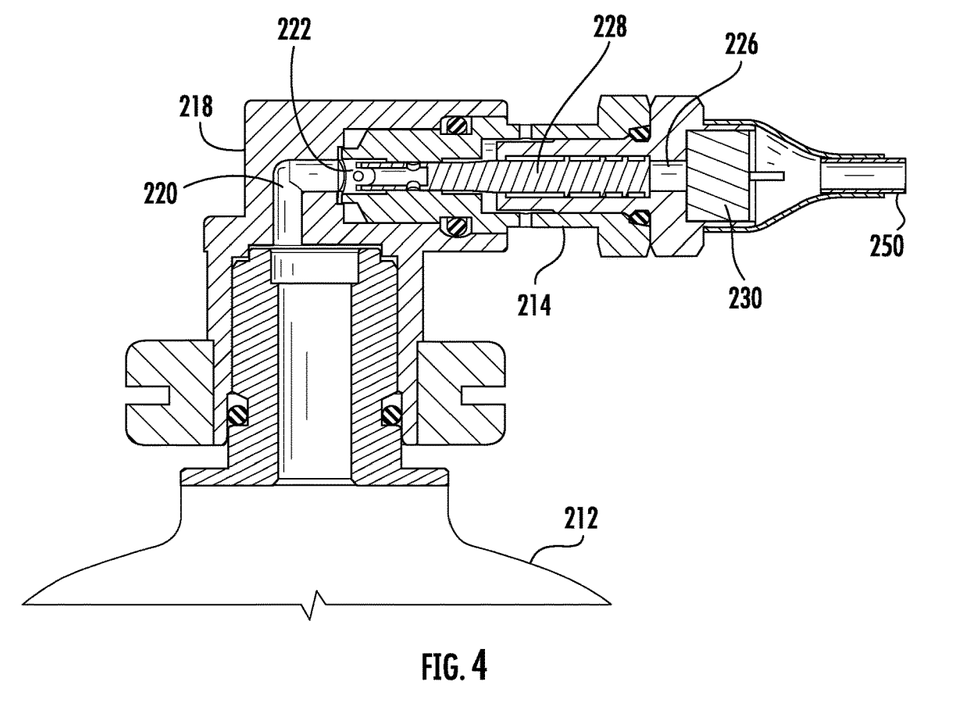
FIG. 4 is an enlarged cross-sectional view of the initiator assembly taken along line 4-4 of FIG. 3.

Referring to FIGS. 3 and 4, storage vessel 212 includes a manifold body 218 attached to the inlet of regulator 216. The manifold body 218 includes a dedicated fill port 215 (see FIG. 3) for filling the vessel 212 with the breathing mixture and defines a first flow passage 220 containing a frangible rupture disc 222. The initiator 214 includes an initiator body 224 defining a second flow passage 226 in fluid communication with the first flow passage 220. A mechanism is provided for rupturing the rupture disc 222 to initiate the flow of oxygen from the storage vessel 212 by way of a flexible low pressure supply tube 250 made from polyurethane or the like.

As shown in FIG. 4, in a preferred embodiment of the subject invention, the mechanism for rupturing the rupture disc 222 includes a tapered brass initiator lance 228 and a pyrotechnic actuator 230 for causing the lance 228 to rupture the disc. Upon sensing a valid first breath, the pulse control module 400 applies power to the pyrotechnic actuator 230 in the high pressure manifold 218. The electrical detonation of the pyrotechnic actuator 230 of the initiator 214 propels the lance 228 to penetrate the rupture disc 222. In the event of an overpressure discharge from the rupture disc 222, the oxygen discharge is directed through a discharge port 232 in the manifold body 218.

Alternatively the mechanism for initiating the flow of oxygen could be a mechanical or spring loaded-lance, or the storage vessel 212 could include a mechanical or solenoid operated valve that is mechanically or electrically moved from a closed positon to an open positon to initiate the flow of oxygen from the storage vessel 212. Preferably, the flow of oxygen from the storage vessel 212 is initiated upon the sensing of a valid first breath by the breath sensor, and in the absence of a valid first breath the initiator 214 is activated.

More particularly, during the activation of the initiator 214, the control module 400 monitors the electrical resistance of the initiator bridge circuit as a means of verifying whether the initiator 214 has been fired successfully. If the control module 400 determines that the initiator has not been fired, the control module 400 will continue to attempt to activate a further 2 times at 5 seconds intervals, after which the initiator 214 is activated by the application of electrical power.

Figure 7:
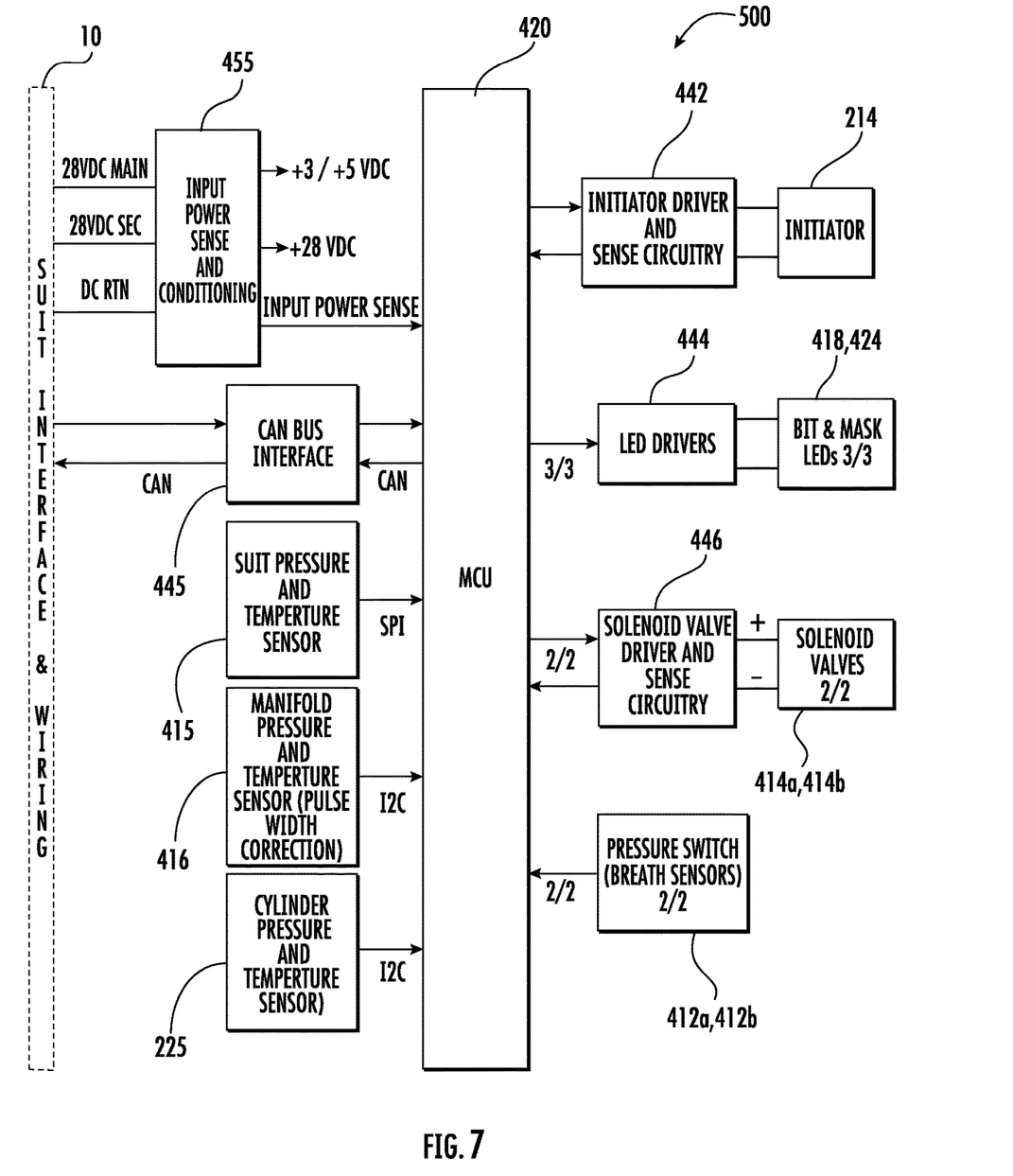
FIG. 7 is a functional block diagram of the oxygen controller assembly with system interfaces.

Referring now to FIG. 2 in conjunction with FIG. 7, the microcontroller unit 420 of pulse control module 400 is in electronic communication with the pressure manifold 410, the source of gaseous oxygen 212 and the pressure suit 10 over an electronic interface 500. The microcontroller unit 420 is programmed to monitor the suit pressure and temperature sensor 415, manifold pressure and temperature sensor 416, and storage vessel pressure and temperature sensor 225. The microcontroller unit 420 is further programmed to manage the initiator 214 and the initiator drivers circuit 442, the BIT and mask LEDs 418, 424 and the LED drivers 444, the breath sensors 412a, 412b and the control valves 414a, 414b and valve driver circuit 446. An electronic interface 445 (e.g., CAN BUS) provides communication between the microcontroller 420 and the pressure suit 10 to exchange data specific to functional test and reporting requirements (e.g., for suit maintenance and health).

The pulse control module 400 is powered continuously by primary and secondary 28 VDC power supplies 450a, 450b, although other voltages could be used. Preferably, power supplies 450a, 450b are isolated and protected from one another by way of an input power sense and conditioning circuit 455 monitored by the MCU 420. Moreover, each power input is transient suppression protected and diode isolated to support segregation requirements at the suit level. These supplies are configured such that any combination of inputs can be used to provide electrical power to the controller 420 by way of a power connector 452, shown in FIG. 6.

The oxygen supply system 100 further includes a Built-In-Test (BIT) functionality. In the event that a valid first breath is not detected in the first 15 seconds after power is applied to the oxygen control module 400 (it is normally unpowered), the oxygen control module 400 will perform a BIT to verify, where feasible, functional aspects of the control module 400 relative to its intended use and operation. If a valid breath is sensed at any time thereafter, the control module 400 will respond by proceeding to activate the initiator 214 to start the flow of oxygen to the pressure manifold 410 of the control module 400. If the supply of oxygen is not controlled by the initiator 214 but using a mechanical or electrical valve, the control module 400 will either signal to electrically open the valve based on the sensing of a valid breath, or act on the presence of oxygen in the case of a mechanical valve. A BIT indicator 424 is provided on the printed circuit board 425, which is illuminated in response to the outcome of the test and it send a message via the CAN connector 426 to report on the condition of the oxygen supply system 100.

The subject invention is also directed to a method for delivering pulsed oxygen to a closed breathing environment, which involves providing a source of gaseous oxygen 200, connecting the source of gaseous oxygen to a phase dilution type oronasal dispensing mask 300 worn by a user in a closed breathing environment defined by a pressure suit 10, and delivering a controlled bolus of oxygen from the source of gaseous oxygen 200 to the oronasal dispensing mask 300 upon demand by the user, wherein the controlled bolus of oxygen is delivered shortly after the start of inhalation.

Figure 8:
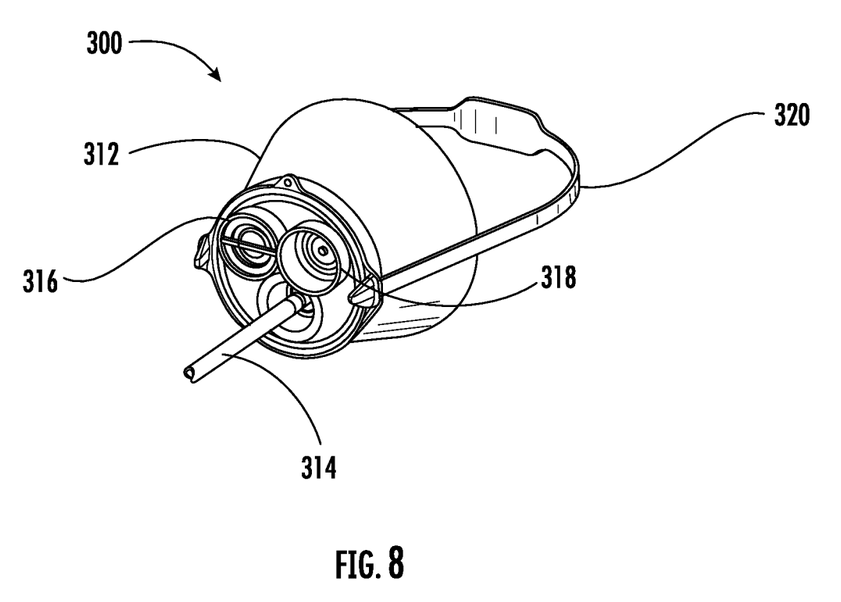
FIG. 8 is a perspective view of phase dilution type oronasal dispensing mask utilized in conjunction with the pulsed oxygen delivery system of the subject invention.

A phase dilution type oronasal dispensing mask 300 is illustrated in FIG. 8 and it includes a conically shaped mask 312 that provides a comfortable seal against the user's nose, cheek and chin areas. The conically shaped mask 312 further includes a strap 320. The mask 312 is fed by a flexible supply tube 314 that communicates with the control module 400. The mask 312 includes an inhalation valve 316, which supports the inhalation phase of the breathing cycle and an exhalation valve 318, which supports the exhalation phase of the breathing cycle.

It is envisioned that bolus volume can be controlled in one or more ways. For example, bolus volume could be controlled according to ambient pressure within the pressure suit, bolus volume could be controlled according to oxygen supply pressure and temperature, and/or bolus volume could be controlled according to a user's level of oxygen blood saturation. Bolus volume could, in addition, also be controlled so as to maintain a user's level of oxygen blood saturation in a target range equal to or greater than a defined baseline percentage specific to the user, so as to optimize the volume of oxygen that is required to be dispensed, as disclosed in U.S. Patent Application Publication No. 2015/0174359. In this regard, the level of blood oxygen saturation could also be measured by an oximeter or similar means and that information could be sent to the microcontroller unit to control the bolus of oxygen delivered to the user.

In situations where the user's measured $SpO_2$ is available as a control input, the oxygen controller 400 employs an operation mode pulse-width look-up table stored in non-volatile memory (NVM) resident in the microprocessor 420. The pulse-width look-up table is indexed such that each $SpO_2$ entry received represents an increment reflecting the desired $SpO_2$ baseline specific to the user. The oxygen controller 400 activates the solenoid valve 414a, 414b for the pulse-width duration determined from the look-up table value corresponding to the index defined from the $SpO_2$ index value received by CAN bus 445. Those skilled in the art will readily appreciate that the paired solenoid valves 414a, 414b are provided for parallel redundancy. In use, only one valve is needed, while the other remains as a "hot" spare if needed.

Compared with unassisted breathing from an ambient oxygen environment, as is the case in current suit systems, the utilization of a pulse delivery of oxygen as disclosed herein is seen as an opportunity to provide the following benefits: offset or improve upon any existing oxygen partial pressure deficiency relative to ground conditions; require less oxygen to be carried to support breathing/workload requirements compared with the current approach; and lower suit pressures which may as a result have a corresponding benefit of reducing physical workload thus leading to a reduction in heat generated and $CO_2$ produced by the occupant that must be accounted for by the environmental control systems and thus, achieve as a result a corresponding reduction in oxygen fire hazard and risk within the suit where the flammability of fuel-like materials is a function of oxygen pressure.

While the subject disclosure has been shown and described with reference to preferred embodiments, those skilled in the art will readily appreciate that changes and/or modifications may be made thereto without departing from the scope of the subject disclosure.

What is claimed is:

1. A pulsed oxygen delivery system for a closed breathing environment defined by a full-body pressure suit configured to enable a wearer to perform extravehicular activities, comprising:
   a) a source of gaseous oxygen;
   b) a phase dilution type oronasal dispensing mask configured to be worn by a user-,
   c) a closed breathing environment defined by the full-body pressure suit, wherein the phase dilution type oronasal dispensing mask is configured to be worn by the user in the closed breathing environment defined by the pressure suit; and
   d) a pulse control module further comprising a microcontroller configured to control and deliver a timed and metered bolus of oxygen from the source of gaseous oxygen to the oronasal dispensing mask upon inhalation by the user.

2. A pulsed oxygen delivery system as recited in claim 1, wherein the pulse control module includes a pressure manifold having one or more breath sensors for sensing a breath taken by the user and one or more control valves for controlling the duration and amount of oxygen delivered to the dispensing mask.

3. A pulsed oxygen delivery system as recited in claim 2, wherein the source of gaseous oxygen includes a pressurized single use or refillable storage vessel, at least one of an initiator comprising a lance, a pyrotechnic actuator, and a rupture disk or a mechanical valve for establishing a flow of oxygen from the storage vessel, and a regulator for managing the delivery of oxygen from the storage vessel to the pressure manifold.

4. A pulsed oxygen delivery system as recited in claim 3, wherein the storage vessel includes a manifold body defining a first flow passage containing a frangible rupture disc, and the initiator includes an initiator body defining a second flow passage in fluid communication with the first flow passage, and wherein, in response to the pyrotechnic actuator actuating the lance, the lance ruptures means are provided for rupturing the rupture disc to initiate the flow of oxygen from the storage vessel to the oronasal dispensing mask by way of a supply tube.

5. A pulsed oxygen delivery system as recited in claim 4, wherein the flow of oxygen from the storage vessel is initiated upon the sensing of a valid first breath by the breath sensor, and in the absence of a valid first breath, the initiator is activated manually by application of electrical power.

6. A pulsed oxygen delivery system as recited in claim 3, wherein the pulse control module includes a microcontroller unit that is in communication with the pressure manifold, the source of gaseous oxygen, and the pressure suit over an electronic interface.

7. A pulsed oxygen delivery system as recited in claim 6, wherein the microcontroller unit is programmed to monitor suit pressure and temperature, manifold pressure and temperature, and storage vessel pressure and temperature.

8. A pulsed oxygen delivery system as recited in claim 7, wherein the microcontroller unit is further programmed to manage the initiator, the one or more control valves, and the one or more breath sensors.

9. A pulsed oxygen delivery system as recited in claim 1, wherein the pulse control module is powered by primary and secondary power supplies that are isolated and protected from one another.

10. A pulsed oxygen delivery system as recited in claim 1, wherein the phase dilution type oronasal dispensing mask includes a flexible supply tube that communicates with the pulse control module, an inhalation valve which supports an inhalation phase of a breathing cycle and an exhalation valve which supports an exhalation phase of the breathing cycle.

11. A method for delivering pulsed oxygen to a closed breathing environment, the closed breathing environment defined by a full-body pressure suit configured to enable a wearer to perform extravehicular activities, comprising:
   a) providing a source of gaseous oxygen;
   b) connecting the source of gaseous oxygen to a phase dilution type oronasal dispensing mask worn by a user in a closed breathing environment defined by the full-body pressure suit; and
   c) delivering a controlled bolus of oxygen from the source of gaseous oxygen to the oronasal dispensing mask upon demand by the user.

12. A method for delivering pulsed oxygen as recited in claim 11, wherein the controlled bolus of oxygen is delivered shortly after the start of inhalation.

13. A method for delivering pulsed oxygen as recited in claim 11, wherein a bolus volume is controlled according to ambient pressure within the pressure suit.

14. A method for delivering pulsed oxygen as recited in claim 11, wherein a bolus volume is controlled according to oxygen supply pressure and temperature.

15. A method for delivering pulsed oxygen as recited in claim 11, wherein a bolus volume is controlled according to a user's level of oxygen blood saturation.

* * * * *

UNITED STATES PATENT AND TRADEMARK OFFICE
CERTIFICATE OF CORRECTION

| | | |
|---|---|---|
| PATENT NO. | : 12,053,654 B2 | |
| APPLICATION NO. | : 17/147162 | |
| DATED | : August 6, 2024 | |
| INVENTOR(S) | : John Terence Barker et al. | |

It is certified that error appears in the above-identified patent and that said Letters Patent is hereby corrected as shown below:

In the Claims

In Claim 4, Column 8, Lines 18-19: please delete the phrase "means are provided for rupturing"

Signed and Sealed this
Nineteenth Day of November, 2024

Katherine Kelly Vidal
*Director of the United States Patent and Trademark Office*